(12) United States Patent
Lutze

(10) Patent No.: US 6,553,824 B1
(45) Date of Patent: Apr. 29, 2003

(54) METHOD FOR DETERMINING PIPETTED VOLUMES OF LIQUID

(75) Inventor: Konstantin Lutze, Hilden (DE)

(73) Assignee: Qiagen GmbH, Hilden (DE)

(*) Notice: Subject to any disclaimer, the term of this patent is extended or adjusted under 35 U.S.C. 154(b) by 0 days.

(21) Appl. No.: 09/646,086
(22) PCT Filed: Mar. 12, 1999
(86) PCT No.: PCT/EP99/01640
§ 371 (c)(1), (2), (4) Date: Sep. 13, 2000
(87) PCT Pub. No.: WO99/47898
PCT Pub. Date: Sep. 23, 1999

(30) Foreign Application Priority Data

Mar. 13, 1998 (DE) .......... 198 10 997

(51) Int. Cl.⁷ ............... G01F 17/00
(52) U.S. Cl. ............... 73/149
(58) Field of Search ............... 73/1.16, 1.36, 73/1.73, 1.74, 863.01, 864.23–864.25, 149; 222/23, 25, 71; 422/100; 340/618

(56) References Cited

U.S. PATENT DOCUMENTS

| | | | |
|---|---|---|---|
| 3,026,705 A | * 3/1962 | Blackman et al. | ............ 73/1.74 |
| 4,331,262 A | * 5/1982 | Snyder et al. | ............ 73/1.36 |
| 4,586,546 A | * 5/1986 | Mezei et al. | |

FOREIGN PATENT DOCUMENTS

| EP | 2 50 671 | * | 1/1988 |
| EP | 0 250 671 B1 | | 1/1992 |
| JP | 60 185134 A | | 9/1985 |
| JP | 6 018 5134 | * | 9/1985 |

* cited by examiner

Primary Examiner—Robert Raevis
(74) Attorney, Agent, or Firm—Leon R. Yankwich

(57) ABSTRACT

A method for determining a volume of liquid is described, wherein the liquid is drawn from a vessel by means of a pipette or is delivered from a pipette into a vessel, respectively. In particular a method is described, wherein as the first step the volume of liquid contained in a vessel $V_{1a}$ is determined by a detector means. Then a volume of liquid $V_{1act}$ is drawn into a pipette and, subsequent thereto, the volume of liquid contained in the vessel $V_{1e}$ is determined again. Thereafter the volume of liquid actually drawn off $V_{1act}$ is calculated in accordance with the equation $V_{1a} - V_{1e} = V_{1act}$. Subsequent thereto the difference between the volume of liquid actually drawn off $V_{1act}$ and a volume of liquid predetermined to be drawn off $V_{1targ}$ is calculated in accordance with the equation $|V_{1act} - V_{1targ}| = V_{1diff}$. Then a comparison of the difference $V_{1diff}$ with a predetermined volume of liquid $\epsilon_1$ is conducted and an error message is displayed in case $V_{1diff} > \epsilon_1$.

11 Claims, 2 Drawing Sheets

METHOD FOR DETERMINING PIPETTED VOLUMES OF LIQUID

CROSS-REFERENCE TO RELATED APPLICATIONS

This application is the National Stage of international application No. PCT/EP99/01640, filed Mar. 12, 1999, which claims priority to German application No. 19810997.0, filed Mar. 13, 1998.

The invention relates to a method for determining a volume of liquid, which is drawn from a vessel by means of a pipette or delivered from a pipette into a vessel, respectively.

Various apparatuses are known which permit the detection of volumes of liquid by determining the level of a calibrated vessel. This may be achieved, for example, by emitting ultrasonic, which is reflected by the surface of the liquid. By determining the period of time elapsed between emitting and receiving the reflected waves the level can be determined. Moreover, conductivity measurements are used for level determination, wherein a probe undergoes a change in conductivity from the point of time of being immersed into a liquid. The prerequisite for applicability of said method being a minimum conductivity of the liquid, the level of which is to be determined.

Within the scope of the present invention a capacity is measured for determining the volume of liquid. In this case a metal surface serves as a first pole, which metal surface is in contact with the vessel, in which the volume of liquid to be detected is located. The second pole is provided by a detector tip, which is moved slowly from above towards the liquid. As is known, the capacity between the two poles is determined by the distance of the same as well as by the medium being located in between. In the moment in which the detector tip is immersed into the liquid, a sudden change of the dielectric constant of the medium being located between the poles takes place, since exactly from this point of time air is excluded from between the two poles. In known automatic pipetting machines the presence of liquids in vessels on the working surface is verified thereby, wherein a too deep immersion of the pipetting needle is prevented.

The above methods for detecting liquids are known from the prior art. The present invention can in general be performed with various of said methods and is thus not limited to the same.

In performing automatic methods for pipetting, a plurality of causes may lead to pipetting errors, such as for example
- obstructions of pipetting tips,
- too early response of the liquid detection by faulty alignment,
- leakage in the hose system,
- leakage in the dilutors.

All causes lead to the fact that a lesser volume of liquid than the actually desired one or, in the extreme case, even no liquid at all is drawn from the vessel into the pipette or is delivered from the pipette into a vessel, respectively. Especially with liquids having a very high steam pressure a response of the liquid detection may be caused already in the gas volume above the liquid, due to the high concentrations prevailing therein.

The drawbacks of the known methods reside in the fact that, during the automatic pipetting process, it is not checked whether liquid has actually been drawn off or delivered, respectively, during the pipetting step and whether the maximum deviation of the pipetted volume from the desired volume is within a predetermined tolerance limit. Pipetting errors are thus not recognized and the attention of the user cannot be drawn to this fact.

The present invention is thus based on the object of providing a method for determining pipetting errors in automatic pipetting processes.

This object is achieved by the invention by the methods specified in independent patent claims 1, 2 and 3 as well as by the apparatuses specified in independent patent claims 8, 9 and 10. Further advantageous details, aspects and embodiments of the invention may be gathered from the dependent patent claims, the description, the figures and the examples.

The above-mentioned object is achieved according to the invention, for example, by a method for determining a volume of liquid, which is drawn from a vessel by means of a pipette, wherein the method comprises the following steps a) through f). As the first step (step a)) the volume of liquid contained in a vessel $V_{1a}$ is determined by a detector means and the value is stored in a computing unit. Then (step b)) a volume of liquid $V_{1act}$ is drawn into a pipette and, subsequent thereto, the volume of liquid contained in the vessel $V_{1e}$ is determined again by a detector means and stored in a computing unit (step c)). Thereafter the calculation of the volume of liquid actually drawn off $V_{1act}$ is conducted by the computing unit in accordance with the equation $V_{1a}-V_{1e}=V_{1act}$ (step d)) Subsequent thereto the difference between the volume of liquid actually drawn off $V_{1act}$ and a volume of liquid predetermined to be drawn off $V_{1targ}$ is calculated by the computing unit in accordance with the equation $|V_{1act}-V_{1targ}|=V_{1diff}$ (step e) Then a comparison of the difference $V_{1diff}$ with a predetermined volume of liquid $\epsilon_1$ is conducted again by the computing unit and an error message is displayed in case $V_{1diff} > \epsilon_1$ (step f))

Furthermore, the invention relates to a method for determining a volume of liquid, which is delivered from a pipette into a vessel, wherein the method comprises the following steps a') through f'). As the first step (step a')) the volume of liquid contained in a vessel $V_{2a}$ is determined by a detector means and the value is stored in a computing unit. Then (step b')) a volume of liquid $V_{2act}$ is delivered from a pipette into the vessel and, subsequent thereto, the volume of liquid contained in the vessel $V_{2e}$ is determined again by a detector means and stored in a computing unit (step c')). Thereafter the calculation of the volume of liquid actually delivered $V_{2act}$ is conducted by the computing unit in accordance with the equation $V_{2e}-V_{2a}=V_{2act}$ (step d')). Subsequent thereto the difference between the volume of liquid actually delivered $V_{2act}$ and a volume of liquid predetermined to be delivered $V_{2targ}$ is calculated by the computing unit in accordance with the equation $|V_{2act}-V_{2targ}|=V_{2diff}$ (step e')). Then a comparison of the difference $V_{2diff}$ with a predetermined volume of liquid $\epsilon_2$ is conducted again by the computing unit and an error message is displayed in case $V_{2diff} > \epsilon_2$.

Moreover, the present invention relates to a method for determining a volume of liquid, which is transferred from a first vessel to a second vessel by means of a pipette. In this method according to the invention firstly the above-mentioned steps a) through f) are performed in order to determine the volume of liquid drawn from the first vessel into the pipette, then the pipette is moved from the first vessel to the second vessel and, subsequent thereto, the above-mentioned steps a') through f') are performed in order to determine the volume of liquid delivered from the pipette into the second vessel. The volume of liquid drawn off from the first vessel may differ from the volume of liquid delivered to the second vessel.

Furthermore, the invention relates to an apparatus for determining a volume of liquid, which is drawn from a vessel by means of a pipette, wherein the apparatus comprises a memory means for storing numerical values, means for determining a volume of liquid contained in the vessel $V_{1a}$, means for drawing a volume of liquid $V_{1act}$ into a pipette, means for determining the volume of liquid contained in the vessel $V_{1e}$, means for calculating the volume of liquid actually drawn off $V_{1act}$ in accordance with the equation $V_{1a} - V_{1e} = V_{1act}$, means for calculating the difference between the volume of liquid actually drawn off $V_{1act}$ and a volume of liquid predetermined to be drawn off $V_{1targ}$ in accordance with the equation $|V_{1act} - V_{1targ}| = V_{1diff}$, means for comparing the difference $V_{1diff}$ with a predetermined volume of liquid $\epsilon_1$ and means for displaying an error message.

Moreover, the present invention comprises an apparatus for determining a volume of liquid, which is delivered from a pipette into a vessel, wherein the apparatus comprises a memory means for storing numerical values, means for determining a volume of liquid contained in the vessel $V_{2a}$, means for delivering a volume of liquid $V_{2act}$ into the vessel, means for determining the volume of liquid contained in the vessel $V_{2e}$, means for calculating the volume of liquid actually delivered $V_{2act}$ in accordance with the equation $V_{2e} - V_{2a} = V_{2act}$, means for calculating the difference between the volume of liquid actually delivered $V_{2act}$ and a volume of liquid predetermined to be delivered $V_{2targ}$ in accordance with the equation $|V_{2act} - V_{2targ}| = V_{2diff}$, means for comparing the difference $V_{2diff}$ with a predetermined volume of liquid $\epsilon_2$ and means for displaying an error message.

Moreover, the invention relates to an apparatus for determining a volume of liquid, which is transferred from a first vessel to a second vessel by means of a pipette, wherein the apparatus comprises the above-mentioned means of the apparatus for determining the volume of liquid drawn from the first vessel into the pipette, furthermore means for moving the pipette from the first vessel to the second vessel and additionally the above-mentioned means of the apparatus for determining the volume of liquid delivered from the pipette into the second vessel.

By means of the present invention it is thus possible to reveal pipetting errors which have not been detectable so far and thus considerably increase the safety of the process. The method according to the invention is particularly applicable in the fields of molecular biology and molecular diagnostics, including purifying and filtering of nucleic acids, in particular plasmid DNA, genomic DNA and RNA, as well as enzymatic reactions and PCR (polymerase chain reaction). However, the present invention is not limited to said fields of application.

Preferred embodiments of the invention will be described in detail in the following. According to an advantageous aspect of the present invention it is possible, in the methods according to the invention for determining the volume of liquid drawn from a vessel, for determining the volume of liquid delivered into a vessel and for determining the volume transferred from a first vessel to a second vessel, to replace step a) or a'), respectively, by use of a value of the volume of liquid contained in the respective vessel $V_{1a}$ or $V_{2a}$, respectively, which value is predetermined by the user.

Another advantageous aspect of the present invention arises from the fact that, subsequent to the above-mentioned step a), steps a1), a2), a3) and a4) are additionally performed. Moreover, subsequent to the determination and storage of the volume of liquid contained in a vessel $V_{1a}$ conducted in step a), the volume of liquid contained in the same vessel is determined again by a detector means, the value is designated $V_{11a}$ and is also stored in a computing unit (step a1)). In case $V_{11a} = 0$ an error message is output (step a2)). Thereafter the difference between $V_{1a}$ and $V_{11a}$ is calculated by the computing unit in accordance with the equation $|V_{1a} - V_{11a}| = V_{11diff}$ (step a3)). Subsequent thereto a comparison of the difference $V_{11diff}$ with a predetermined volume of liquid $\epsilon_{11}$ is conducted by the computing unit and in case $V_{11diff} > \epsilon_{11}$ an error message is displayed (step a4)).

According an especially advantageous aspect of the present invention the volume of liquid drawn from the first vessel into the pipette $V_{1targ}$ or the volume of liquid delivered from the pipette into the second vessel $V_{2targ}$ fulfils the condition 1 $\mu l < (V_{1targ}; V_{2targ}) < 10000$ $\mu l$, preferably the condition 10 $\mu l < (V_{1targ}; V_{2targ}) < 1000$ $\mu l$ and most preferably the condition 100 $\mu l < (V_{1targ}; V_{2targ}) < 400$ $\mu l$.

A further preferred aspect of the present invention is realized in that a detector tip, which is used as the detector means, is immersed into the liquid prior to at least one determination of the volume of liquid and is subsequently moved back in a position above the surface of the liquid. By immersing the detector tip prior to detecting the surface of the liquid faulty determinations can be avoided, which are caused by drops of liquid present at the detector tip. Said drops can be stripped off by the immersion which enables a fault-free detection subsequent thereto. Preferably, the immersing step can be performed several times. The described method for stripping off drops of liquid from the detector tip may also be performed in determinations of volume, which are not related to the determination of volumes delivered or drawn off, respectively.

After outputting an error message during the method according to the invention an error treatment is conducted, which is, however, dependent on the particular application and thus independent of the present invention. For this reason, the error treatment is not described in greater detail herein.

The method according to the invention will be described in greater detail by means of the following example and with reference to the figures, even though the invention is not limited thereto.

EXAMPLE

Figure 1A:
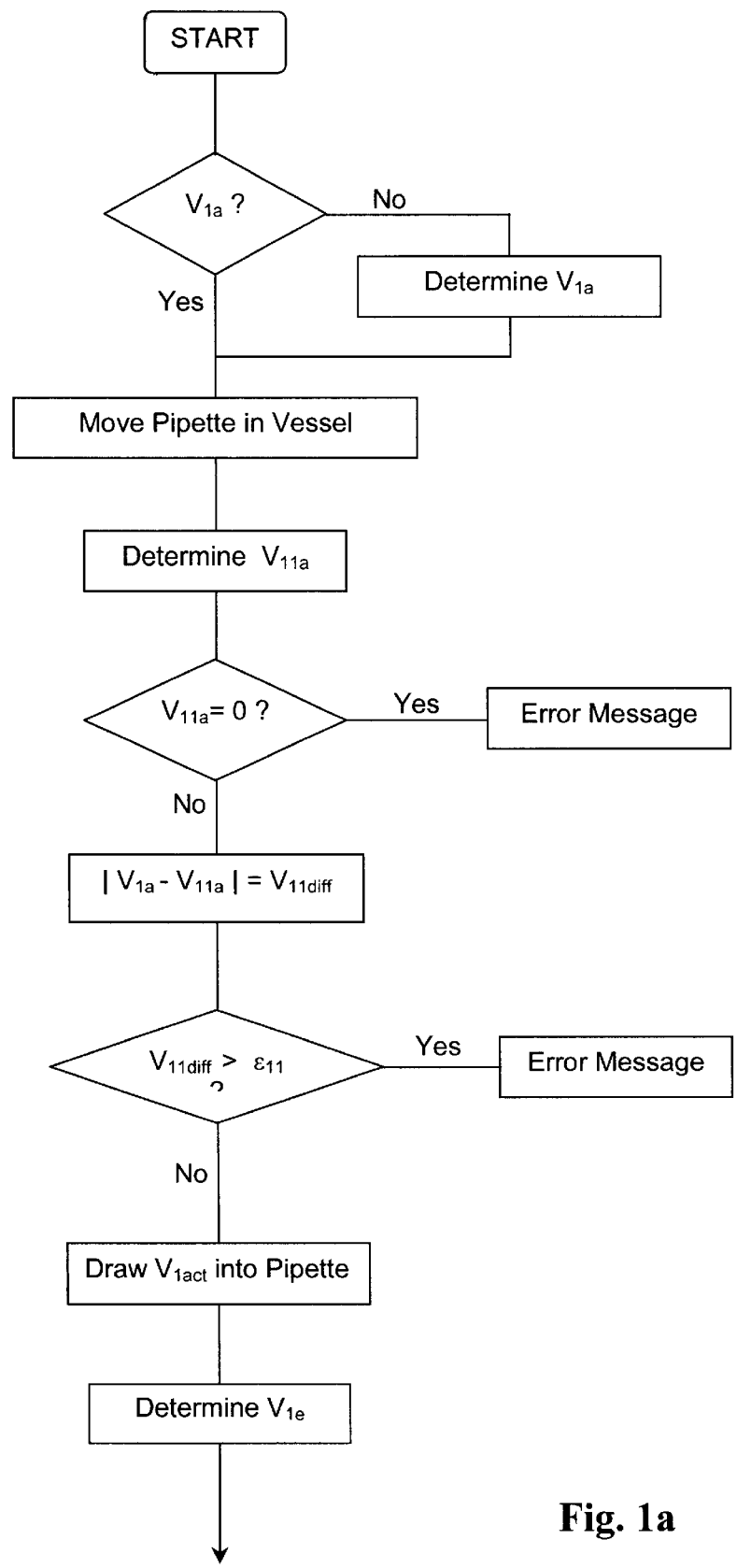
FIG. 1a and FIG. 1b together depict a flow chant illustrating the steps of a preferred method according to the present invention.

By means of the flow chart shown in FIGS. 1a and 1b a particular embodiment of the present invention will now be explained in greater detail. After starting the method, the level $V_{1a}$ of a first vessel is detected. The level can either be input into a computing unit by a user or, in case this has not been done, be detected by performing a measurement by means of liquid detection. If a command to transfer a volume of liquid by pipetting is now input in the computing unit, then the detector tip is moved in the first vessel, the surface of the liquid is detected and the volume of liquid $V_{11a}$ is thus determined. In case $V_{11a} = 0$, i.e. there is no liquid present in the vessel, then an error message is output. Thereafter the difference between $V_{1a}$ and $V_{11a}$ is calculated by the computing unit in accordance with the equation $|V_{1a} - V_{11a}| = V_{11diff}$. Subsequent thereto a comparison of the difference $V_{11diff}$ with a predetermined volume of liquid $\epsilon_1$ is conducted by the computing unit and, in case $V_{11diff} > \epsilon_{11}$, an error message is displayed. If $V_{11diff}$ is within the interval predetermined by $\epsilon_{11}$, i.e. $V_{11diff}<\epsilon_{11}$, then a volume of liquid $V_{1act}$ is drawn into the pipette. During drawing off liquid the pipette is preferably lowered a short additional distance further downwards into the liquid in order to prevent intake of air. Then the volume of liquid $V_{1act}$ is drawn into the pipette, wherein, during drawing off liquid, the pipette is permanently moved downwards into the liquid, whereby intake of air is prevented as the level decreases. Subsequently, the volume of liquid contained in the vessel $V_{1e}$ is determined and stored in a computing unit.

Figure 1B:
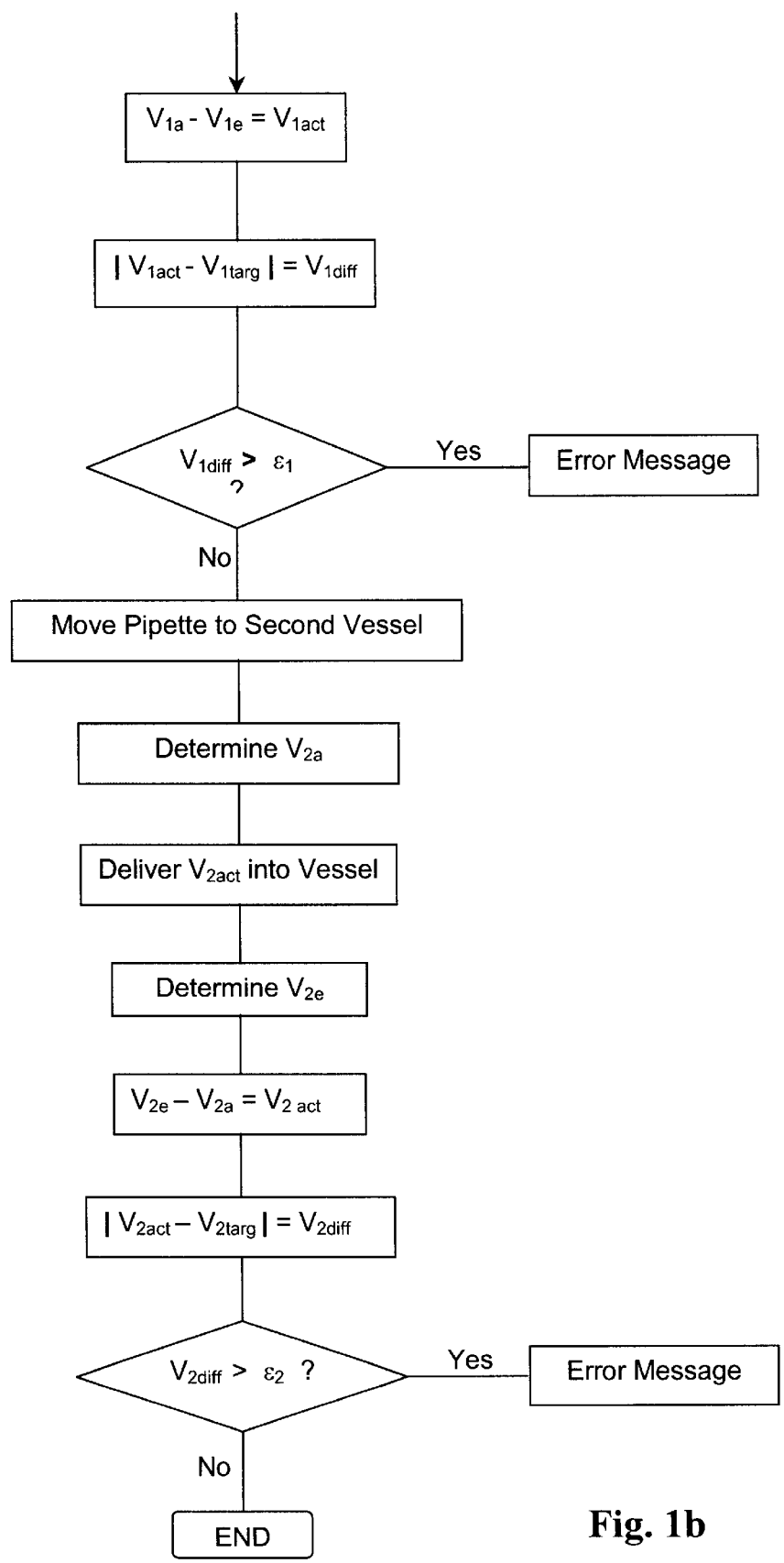

Thereafter the calculation of the volume of liquid actually drawn off $V_{1act}$ is conducted by the computing unit in accordance with the equation $V_{1a}-V_{1e}=V_{1act}$ (cf. FIG. 1b). Subsequent thereto the difference between the volume of liquid actually drawn off $V_{1act}$ and a volume of liquid predetermined to be drawn off $V_{1targ}$ is calculated by the computing unit in accordance with the equation $|V_{1act}-V_{1targ}|=V_{1diff}$. Then a comparison of the difference $V_{1diff}$ with a predetermined volume of liquid $\epsilon_1$ is conducted again by the computing unit and an error message is displayed in case $V_{1diff}>\epsilon_1$. If $V_{1diff}$ is within the interval predetermined by $\epsilon_1$, i.e. $V_{1diff}<\epsilon_1$, then the pipette is moved from the first vessel to the second vessel. As the next step the volume of liquid contained in the second vessel $V_{2a}$ is determined and the value is stored in a computing unit. Then a volume of liquid contained in the pipette $V_{2act}$ is delivered from the pipette into the second vessel and, subsequent thereto, the volume of liquid contained in the second vessel $V_{2e}$ is determined again and stored in a computing unit. Thereafter the calculation of the volume of liquid actually delivered $V_{2act}$ is conducted by the computing unit in accordance with the equation $V_{2e}-V_{2a}=V_{2act}$. Subsequent thereto the difference between the volume of liquid actually delivered $V_{2act}$ and a volume of liquid predetermined to be delivered $V_{2targ}$ is determined by the computing unit in accordance with the equation $|V_{2act}-V_{2targ}|=V_{2diff}$. Then in turn a comparison of the difference $V_{2diff}$ with a predetermined volume of liquid $\epsilon_2$ is conducted again by the computing unit and an error message is displayed in case $V_{2diff}>\epsilon_2$. If $V_{2diff}$ is within the interval predetermined by $\epsilon_2$, i.e. $V_{2diff}<\epsilon_2$, then the method is completed.

What is claimed is:

1. Method for determining a volume of liquid, which is drawn from a vessel by means of a pipette, wherein the method comprises the following steps:
   a) determining a volume of liquid contained in the vessel $V_{1a}$ by a detector means and storing the value in a computing unit;
   b) drawing a volume of liquid $V_{act}$ into a pipette;
   c) determining the volume of liquid contained in the vessel $V_{1e}$ by a detector means and storing the value in a computing unit;
   d) calculating the volume of liquid actually drawn off $V_{1act}$ by means of the computing unit in accordance with the equation $$V_{1a}-V_{1e}=V_{1act};$$

e) calculating the difference between the volume of liquid actually drawn off $V_{1act}$ and a volume of liquid predetermined to be drawn off $V_{1targ}$ by means of the computing unit in accordance with the equation $$|V_{1act}-V_{1targ}|=V_{1diff};$$

f) comparing the difference $V_{1diff}$ with a predetermined volume of liquid $\epsilon_1$ by means of the computing unit and displaying an error message in case $V_{1diff}>\epsilon_1$.

2. Method for determining a volume of liquid, which is delivered from a pipette into a vessel, wherein the method comprises the following steps:
   a') determining a volume of liquid contained in the vessel $V_{2a}$ by a detector means and storing the value in a computing unit;
   b') delivering a volume of liquid $V_{2act}$ into the vessel;
   c') determining the volume of liquid contained in the vessel $V_{2e}$ by a detector means and storing the value in a computing unit;
   d') calculating the volume of liquid actually delivered $V_{2act}$ by means of the computing unit in accordance with the equation $$V_{2e}-V_{2a}=V_{2act};$$

e') calculating the difference between the volume of liquid actually delivered $V_{2act}$ and a volume of liquid predetermined to be delivered $V_{2targ}$ by means of the computing unit in accordance with the equation $$|V_{2act}-V_{2targ}|=V_{2diff};$$

f') comparing the difference $V_{2diff}$ with a predetermined volume of liquid $\epsilon_2$ by means of the computing unit and displaying an error message in case $V_{2diff}>\epsilon_2$.

3. Method for determining a volume of liquid, which is transferred from a first vessel to a second vessel by means of a pipette, said method comprising the steps of:
   a) determining a volume of liquid contained in the vessel $V_{1a}$ by a detector means and storing the value in a computing unit;
   b) drawing a volume of liquid $V_{act}$ into a pipette;
   c) determining the volume of liquid contained in the vessel $V_{1e}$ by a detector means and storing the value in a computing unit;
   d) calculating the volume of liquid actually drawn off $V_{1act}$ by means of the computing unit in accordance with the equation $$V_{1a}-V_{1e}=V_{1act};$$

e) calculating the difference between the volume of liquid actually drawn off $V_{1act}$ and a volume of liquid predetermined to be drawn off $V_{1targ}$ by means of the computing unit in accordance with the equation $$|V_{1act}-V_{1targ}|=V_{1diff};$$

f) comparing the difference $V_{1diff}$ with a predetermined volume of liquid $\epsilon_1$ by means of the computing unit and displaying an error message in case $V_{1diff}>\epsilon_1$, wherein the pipette is then moved from the first vessel to the second vessel, and, subsequent thereto, the following steps are performed in order to determine volume of liquid delivered from the pipette into the second vessel:
   a') determining a volume of liquid contained in the vessel $V_{2a}$ by a detector means and storing the value in a computing unit;
   b') delivering a volume of liquid $V_{2act}$ into the vessel;
   c') determining the volume of liquid contained in the vessel $V_{2e}$ by a detector means and storing the value in a computing unit;
   d') calculating the volume of liquid actually delivered $V_{2act}$ by means of the computing unit in accordance with the equation $$V_{2e}-V_{2a}=V_{2act};$$

e') calculating the difference between the volume of liquid actually delivered $V_{2act}$ and a volume of liquid predetermined to be delivered $V_{2targ}$ by means of the computing unit in accordance with the equation $$|V_{2act}-V_{2targ}|=V_{2diff};$$

f) comparing the difference $V_{2diff}$ with a predetermined volume of liquid $\epsilon_2$ by means of the computing unit and displaying an error message in case $V_{2diff} > \epsilon_2$.

4. Method according any one of claims 1 to 3, wherein as step a) or step a'), respectively, the value of the volume of liquid contained in the vessel $V_{1a}$ or $V_{2a}$, respectively, is predetermined by the user.

5. Method according to claim 1 or 3, wherein subsequent to step a) the following steps are additionally performed:
   a1) determining the volume of liquid contained in the first vessel $V_{11a}$ by a detector means and storing the value in a computing unit;
   a2) outputting an error message in case $V_{11a}=0$;
   a3) calculating the difference between $V_{1a}$ and $V_{11a}$ by means of the computing unit in accordance with the equation $$|V_{1a}-V_{11a}|=V_{11diff};$$

a4) comparing the difference $V_{11diff}$ with a predetermined volume of liquid $\epsilon_{11}$ by means of the computing unit and displaying an error message in case $V_{11diff} > \epsilon_{11}$.

6. Method according to claim 4, wherein the volume of liquid drawn from the first vessel into the pipette or delivered from the pipette into the second vessel, respectively, $V_{1targ}$ or $V_{2targ}$, respectively, fulfils the condition $$1 \, \mu l < (V_{1targ}; V_{2targ}) < 10000 \, \mu l$$

preferably $$10 \, \mu l < (V_{1targ}; V_{2targ}) < 1000 \, \mu l$$

most preferably $$100 \, \mu l < (V_{1targ}; V_{2targ}) < 400 \, \mu l.$$

7. Method according to claim 6, wherein prior to determining at least one volume of liquid a detector tip, which is used as the detector means, is at least once immersed into the liquid and is subsequently moved back in a position above the surface of the liquid.

8. Apparatus for determining a volume of liquid, which is drawn from a vessel by means of a pipette, wherein the apparatus comprises the following means:
   a) memory means for storing numerical values;
   b) means for determining a volume of liquid contained in the vessel $V_{1a}$;
   c) means for drawing a volume of liquid $V_{1act}$ into a pipette;
   d) means for determining the volume of liquid contained in the vessel $V_{1e}$;
   e) means for calculating the volume of liquid actually drawn off $V_{1act}$ in accordance with the equation $$V_{1a}-V_{1e}=V_{1act};$$

f) means for calculating the difference between the volume of liquid actually drawn off $V_{1act}$ and a volume of liquid predetermined to be drawn off $V_{1targ}$ in accordance with the equation $$|V_{1act}-V_{1targ}|=V_{1diff};$$

g) means for comparing the difference $V_{1diff}$ with a predetermined volume of liquid $\epsilon_1$;
   h) means for displaying an error message.

9. Apparatus for determining a volume of liquid, which is delivered from a pipette into a vessel, wherein the apparatus comprises the following means:
   a') memory means for storing numerical values;
   b') means for determining a volume of liquid contained in the vessel $V_{2a}$;
   c') means for delivering a volume of liquid $V_{2act}$ into the vessel;
   d') means for determining the volume of liquid contained in the vessel $V_{2e}$;
   e') means for calculating the volume of liquid actually delivered $V_{2act}$ in accordance with the equation $$V_{2e}-V_{2a}=V_{2act};$$

f') means for calculating the difference between the volume of liquid actually delivered $V_{2act}$ and a volume of liquid predetermined to be delivered $V_{targ}$ in accordance with the equation $$|V_{2act}-V_{2targ}|=V_{2diff};$$

g') means for comparing the difference $V_{2diff}$ with a predetermined volume of liquid $\epsilon_2$;
   h') means for displaying an error message.

10. Apparatus for determining a volume of liquid, which is transferred from a first vessel to a second vessel by means of a pipette, wherein the apparatus comprises:
   A) means for determining the volume of liquid drawn from the first vessel into the pipette, comprising
      i) memory means for storing numerical values;
      ii) means for determining a volume of liquid contained in the vessel $V_{1a}$;
      iii) means for drawing a volume of liquid $V_{1act}$ into a pipette;
      iv) means for determining the volume of liquid contained in the vessel $V_{1e}$;
      v) means for calculating the volume of liquid actually drawn off $V_{1act}$ in accordance with the equation $$V_{1a}-V_{1e}=V_{1act};$$

vi) means for calculating the difference between the volume of liquid actually drawn off $V_{1act}$ and a volume of liquid predetermined to be drawn off $V_{1targ}$ in accordance with the equation $$|V_{1act}-V_{1targ}|=V_{1diff};$$

vii) means for comparing the difference $V_{1diff}$ with a predetermined volume of liquid $\epsilon_1$;
      viii) means for displaying an error message; and
   B) a means for moving the pipette from the first vessel to the second vessel; and
   C) means for determining the volume of liquid delivered from the pipette into the second vessel comprising:
      a') memory means for storing numerical values;
      b') means for determining a volume of liquid contained in the vessel $V_{2a}$;

c') means for delivering a volume of liquid $V_{2act}$ into the vessel;

d') means for determining the volume of liquid contained in the vessel $V_{2e}$;

e') means for calculating the volume of liquid actually delivered $V_{2act}$ in accordance with the equation $$V_{2e} - V_{2a} = V_{2act};$$

f') means for calculating the difference between the volume of liquid actually delivered $V_{2act}$ and a volume of liquid predetermined to be delivered $V_{targ}$ in accordance with the equation $$|V_{2act} - V_{2targ}| = V_{2diff};$$

g') means for comparing the difference $V_{2diff}$ with a predetermined volume of liquid $\epsilon_2$;

h') means for displaying an error message.

11. Method according to claim 5, wherein prior to determining at least one volume of liquid a detector tip, which is used as the detector means, is at least once immersed into the liquid and is subsequently moved back in a position above the surface of the liquid.

* * * * *